United States Patent [19]

Boute et al.

[11] Patent Number: 4,539,991
[45] Date of Patent: Sep. 10, 1985

[54] DUAL CHAMBER PACEMAKER

[75] Inventors: Wim Boute, Doesburg; Frederik H. M. Wittkampf, Brummen; Gerrit W. van Arragon, Dieren, all of Netherlands

[73] Assignee: Vitafin N.V., Curacao, Netherlands Antilles

[21] Appl. No.: 465,890

[22] Filed: Feb. 11, 1983

[51] Int. Cl.$^3$ .............................................. A61N 1/30
[52] U.S. Cl. .............................................. 128/419 PG
[58] Field of Search .................................. 128/419 PG

[56] References Cited

U.S. PATENT DOCUMENTS

| 3,903,897 | 9/1975 | Woolons et al. | 128/419 PG |
| 3,942,534 | 3/1976 | Allen et al. | 128/419 PG |
| 4,059,116 | 11/1977 | Adams | 128/419 PG |
| 4,163,451 | 8/1979 | Lesnick et al. | 128/419 PG |
| 4,421,114 | 12/1983 | Berkovits et al. | 128/419 PG |
| 4,452,248 | 6/1984 | Keller, Jr. | 128/419 PG |

FOREIGN PATENT DOCUMENTS

| 0050038 | 4/1982 | European Pat. Off. | |
| WO82/48211 | 11/1982 | PCT Int'l Appl. | 128/419 PG |

*Primary Examiner*—William E. Kamm
*Attorney, Agent, or Firm*—Woodcock, Washburn, Kurtz, Mackiewicz & Norris

[57] ABSTRACT

An improved cardiac pacemaker adapted to be programmed into one of a plurality of given modes of operation, including dual chamber modes, and in particular synchronous operation for pacing the patient's ventricle following detection of natural atrial heartbeats. The pacemaker has means for monitoring the time relationship between delivered ventricular stimulus pulses and next succeeding atrial heartbeats, for determining the occurrence of pacemaker induced retrograde P waves, or pacemaker caused tachycardia. The timing, and thus the rate of sensed P signals is processed to determine the desirability of establishing a special P sense window for looking for the occurrence of P signals at rates above a normal maximum operating rate, in which event the stability of the V-A timing is monitored in accordance with predetermined criteria to determine the existence of pacemaker mediated tachycardia, which may be broken up by skipping a ventricular stimulus. During detection of atrial beats at a rate higher then the predetermined maximum operating rate, the synchronous ventricular stimulus rate is maintained at an average at or below the maximum rate, while maintaining a substantially constant A-V interval.

24 Claims, 7 Drawing Figures

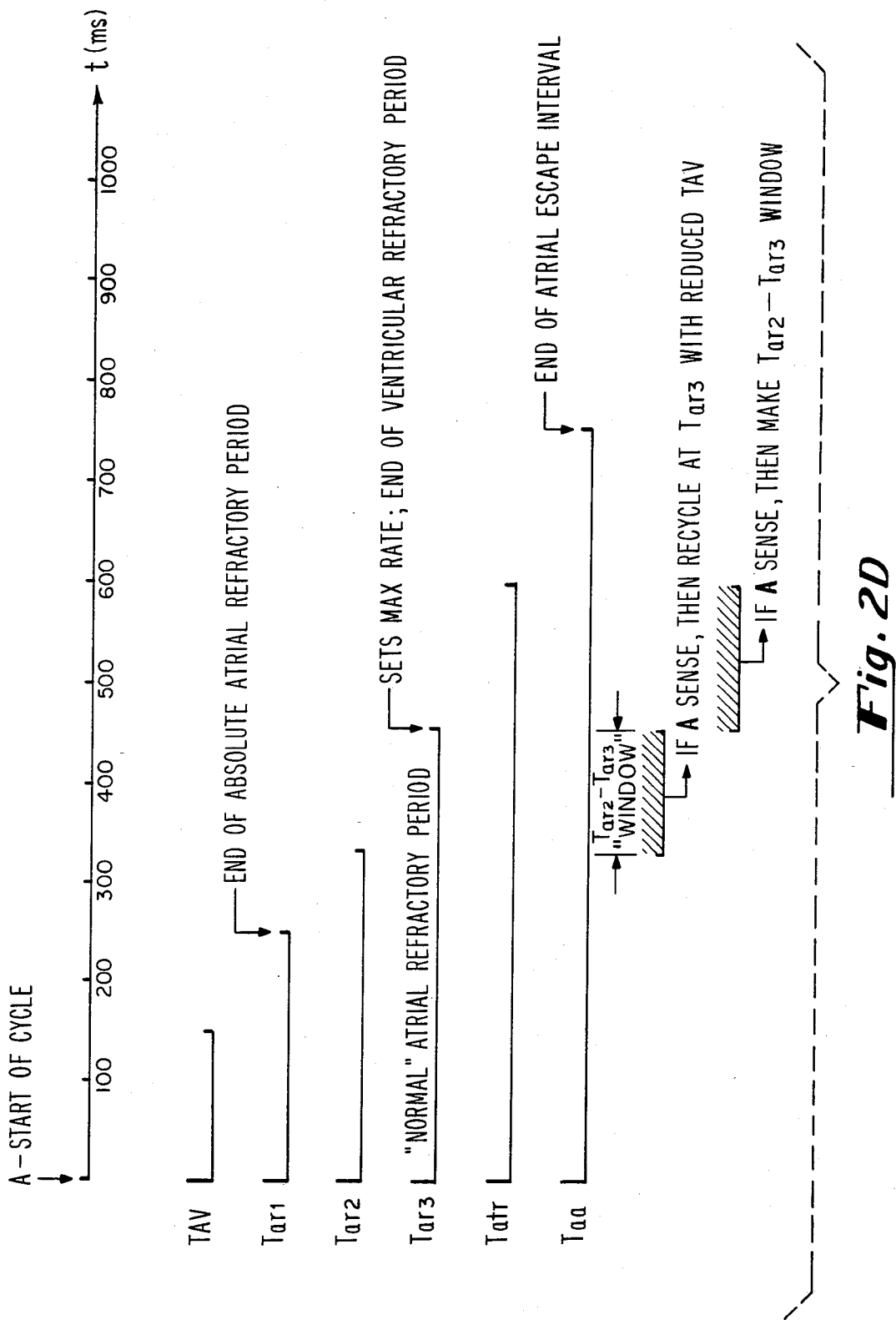

DUAL CHAMBER PACEMAKER

BACKGROUND OF THE INVENTION

This invention relates to cardiac pacemakers and, more particularly, to dual chamber cardiac pacemakers adapted to be operated in a plurality of operating modes, including a mode which incorporates P wave synchronous operation, e.g. VDD, DDD.

The advantages of cardiac pacing in different modes, selected to different patient conditions, is now well recognized in the art. Early pacer systems were solely ventricular, which was sufficient for management of patients with complete heart block and Stokes-Adams attacks. However, ventricular pacemakers, even when demand pacemakers, are not equipped to take advantage of atrial activity, and thus are limited in their efficiency. Subsequently, artrial synchronous, ventricular pacemakers were introduced, having a lead for sensing P signals from the atrium and another for pacing the ventricle after a suitable P-R (A-V) interval. Such a pacemaker, e.g. VDI or VDD, allows the atrium to control the heart's response rate, the ventricle being paced at the atrial rate up to a predetermined upper rate limit. Such synchronous pacers have incorporated means for pacing the ventricle at a 1:2 rate relative to the atrium, or even higher ratio, when the sensed atrial rate exceeds the predetermined maximum rate.

Another form of A-V, or dual chamber pacer that has been utilized is the sequential pacemaker (DVI), which paces both the atrium and the ventricle with an appropriate A-V delay which is timed by the pacemaker. Other pacing modes have been developed, and are classified in accordance with the commonly adopted ICHD code system. In this classification system, the first letter represents the chamber(s) paced (A for atrium; V for ventricle; D for dual), the second letter represents the chamber(s) sensed, and the third letter represents the sensing function, i.e. inhibited (I), trigger (T), dual (D). Known pacing modes include AAI, AAT, VAT, VDD, VDI, VVI, VDD, DVI, VVI, DDT, and DDD. Other codes are used to represent programmability and means for dealing with tachycardia.

With the advent of programmability of pacemakers, as well as improved lead systems for transmitting electrical signals to and from the atrium as well as the ventricle, dual chamber modes of operation are becoming more common and are expected to receive increased use. The advantages of the DDD, or universal pacer, are being more widely considered. In plural operating mode systems, which include P wave (or atrial) synchronous operation, it has been known that pacemaker induced, or mediated tachycardia can be a problem. The problem is caused by the retrograde transmission from the ventricle to the atrium of an electrical signal due to a delivered ventricular stimulus pulse, thereby inducing a retrograde P wave. If the pacemaker is permitted to carry on over too great a number of cycles, wherein retrograde P waves follow delivered stimulus pulses, a dangerous pacemaker mediated, i.e. supported, tachycardia results, which should somehow be controlled.

Another problem that exists in operating in any mode which involves P wave synchronous operation originates from attempts to maintain ventricular pacing at a rate no greater than a predetermined maximum rate, even when the natural atrial signal is above such rate. One prior art means of achieving this is to effectively extend the A-V interval for a number of pacer cycles, so that the pacing rate does not exceed the predetermined maximum during those cycles, and then occasionally skip a ventricular pulse and come back into normal synchronous operation. However, this means of operation carries the risk of excessively long actual A-V times, which can have a detrimental effect, including establishing conditions favorable to pacemaker mediated tachycardia.

SUMMARY OF THE INVENTION

It is an object of this invention to provide an improved dual chamber pacemaker, having means for detecting and breaking up pacemaker induced tachycardia.

It is another object of this invention to provide a pacemaker system having an improved method of monitoring the occurrence of retrograde P waves, and a method and means for altering pacemaker performance so as to discontinue or alter pacing in such a way as to avoid and break up pacemaker supported tachycardia characterized by retrograde P waves.

It is another object of this invention to provide a programmable cardiac pacemaker, having one or more modes which include A-V synchronous operation, having means for improved synchronous pacing under circumstances where the natural atrial rate exceeds a predetermined pacer maximum rate, while maintaining a substantially stable A-V delay for delivered ventricular stimulus pulses.

It is a further object of this invention to provide a pacemaker adaptable for dual chamber operation, having improved means of high rate A-V operation, including determining when a sensed high atrial rate is physiological or not.

It is another object of this invention to provide a pacing system having means for measuring the stability of the V-A interval during synchronous operation, and for making a determination of pacemaker induced or mediated tachycardia on the basis thereof.

It is another object of this invention to provide a pacemaker having improved means for altering the pacemaker operation at rates above a predetermined high frequency limit, in order to achieve improved high rate synchronous operation.

It is another object of this invention to provide a cardiac pacemaker with means for controlling synchronous opertion when the natural atrial rate of the patient is detected to be above a predetermined high rate limit, having improved means for processing sensed atrial rate changes to control the pacemaker to go into an altered high rate operation.

In accordance with the above objects, there is provided a programmable dual chamber cardiac pacemaker, having means for synchronous pacing, having the improvement of means for monitoring the V-A stability of paced operation, and for determining as a function of said monitoring the existence of pacemaker mediated tachycardia due to retrograde P waves. Means are provided for breaking up the pacemaker induced tachycardia, such as by skipping a ventricular stimulus which would normally be delivered in synchronous response to a sensed P signal. The pacer also provides improved means for limiting the mean rate of ventricular stimulation when the sensed atrial rate exceeds a predetermined maximum limit, while maintaining a substantially stable real A-V time out interval for all delivered ventricular stimulus pulses.

BRIEF DESCRIPTION OF THE DRAWINGS

FIG. 2D is a graph illustrating time intervals timed out during each pacer cycle of the pacemaker of this invention.

DESCRIPTION OF THE PREFERRED EMBODIMENTS

In the following description of dual chamber pacemaker operation, the letters P and A are used interchangably. P is normally used to represent the P wave portion of the ECG signal, whereas A is used more broadly to describe an atrial signal, either a sensed atrial beat (P signal) or delivered atrial stimulus pulse. The term "synchronous" operation refers to P wave synchronous operation, wherein a generated ventricular stimulus pulse is timed to be delivered to the ventricle following a given delay ($T_{AV}$) after the sensed P signal. Such synchronous operation takes pace in, for example, the VDD and DDD pacemaker types of operation.

Figure 1:
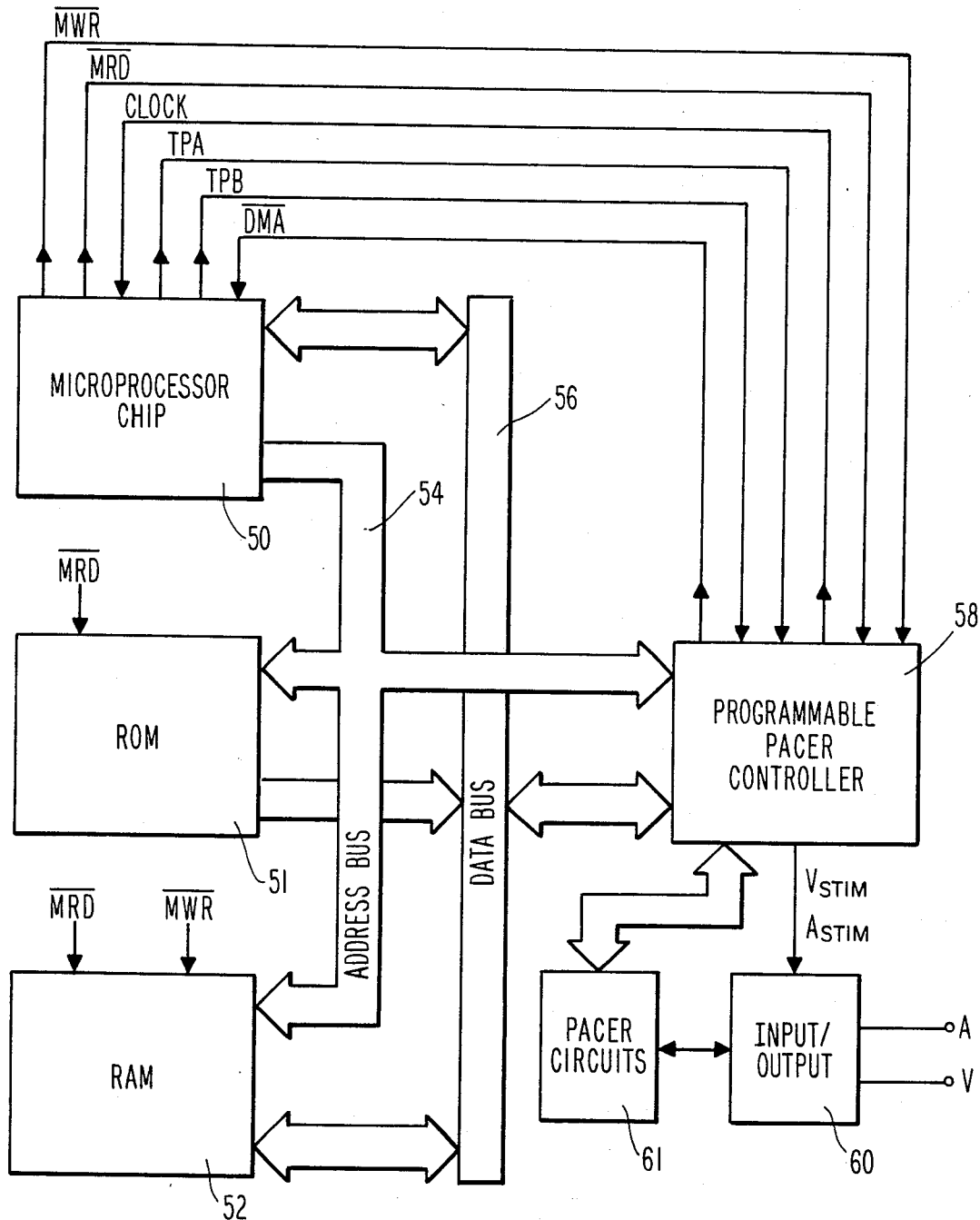
FIG. 1 is an overall block diagram of the pacemaker system of this invention, showing the primary pacemaker system components as used in practicing the method of this invention.

Referring now to FIG. 1, there is shown a block diagram of the primary components of the apparatus of this invention. Shown in block 50 is a microprocessor chip, and as used hereinafter the term microprocessor or microprocessor element means a commercially available microprocessor, whether of one or more chips. A preferred microprocessor for use in the application of this invention as part of a programmable cardiac pacer is the CDP 1802 microprocessor made by RCA. The CDP 1802, hereinafter the 1802, is fabricated on a single chip utilizing a silicon gate CMOS structure. Because of its CMOS structure it offers the design advantages of wide operating temperature range, relatively high speed, high noise immunity and in particular low power consumption. It is to be understood that particularly for an implantable pacer application, where the lifetime of a battery source is important, a low power CMOS microprocessor is particularly advantageous . Other microprocessors are suitable for use in this invention, including the Hitachi 8080A.

Descriptions and specifications of the CDP 1802 are freely available and in the technical literature, and accordingly a full description of the microprocessor is not necessary in this specificaton. However, some further comments are useful for clarifying the description of this invention. The CDP 1802 has a 40 pin circuit. A standard bidirectional parallel data bus 56 utilizes 8 pins, BUS 0-BUS 7. All parallel data communications between the CPU and external logic, memory or I/O occur via this data bus. There is an 8 bit address bus, represented by the numeral 54. All addresses must be multiplexed; the high order address byte is first outputted, followed by the low order address byte. It is to be noted that compatible memory is used with the CDP 1802 which includes address decode logic. There are 7 status flag pins, including Data Flag and Interrupt Enable Flag, 4 I/O flags and a Q Status Flag which can be set or reset directly by appropriate instructions. There are 4 timing signals, namely CLOCK, $\overline{XTAL}$, TPA and TPB. CLOCK is the principle timing signal, inputted from a clock found in programmable pacer controller 58 and controlled by logic within that controller. The frequency of the clock can be up to 6.4 MHz, but for this application may be about 40 KHz. When using the on-chip clock logic of the microprocessor, an external crystal must be connected with a parallel resistor to the $\overline{XTAL}$ and clock pins. TPA and TPB are timing pulses output by the microprocessor each machine cycle, to control external logic. The remaining pins are control pins, only three of which are illustrated here. $\overline{MWR}$ and $\overline{MRD}$ control the memory operation. $\overline{MWR}$ is output as a low pulse after the second (low order) byte of an address has been paced on the address bus. $\overline{MWR}$ indicates a memory access opertion. $\overline{MRD}$ indicates the direction of data access; if $\overline{MRD}$ is low, then the microprocessor is reading data from memory or I/O devices, while if MRD is high, then the microprocessor is writing to memory or I/O devices. The remaining control line shown connected to a pin of the microprocessor is $\overline{DMA}$, for DMA operation.

Still referring to FIG. 1, the address bus 54 is shown interconnected with ROM memory 51, RAM memory 52, and the programmable pacer controller circuit 58. The ROM is suitably an RCA model CPD 1833 chip or equivalent, while the RAM is suitably an RCA model CDP 1822 chip or equivalent. The data bus 56 interconnects the microprocessor chip 50 with ROM 51, RAM 52 and pacer controller 58. Although only one ROM and one RAM block are shown, it is to be understood that there is no limitation on the amount of memory, subject only to design considerations. As further shown in FIG. 1, timing signals represented as $V_{stim}$ and $A_{stim}$ are connected from controller 58 to a conventional output stage which is part of input/output block 60, for developing an output signal to be delivered to a patient's heart. Sensed P and R waves are inputted from block 60 to circuits 61. It is to be understood that for a pacer application other conventional circuitry is incorporated, including timing logic for determining the rate and circumstances for delivering output pulses; A and V sense paths for processing inputted heart signals; receiving means for receiving external program signals and modifying operating parameters in accordance with such external signal; etc. All these functions are conventional and well described in the patent literature, and are represented by block 61 which is shown communicating with controller 58 and input/output block 60.

Figure 2A:
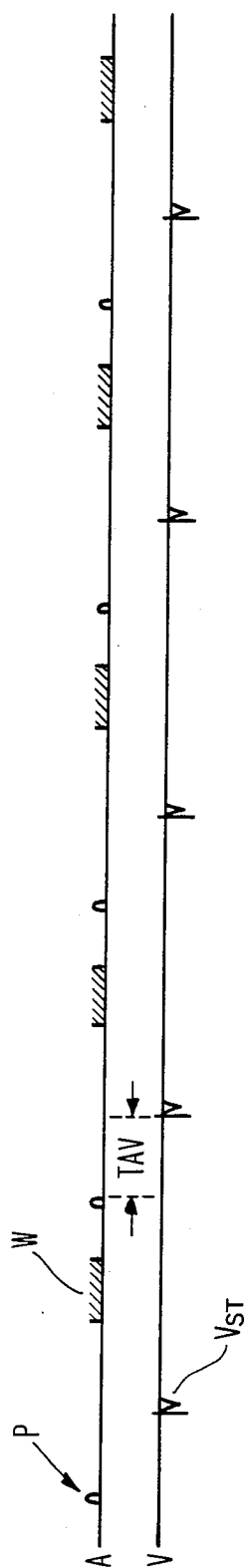
FIG. 2A is an A/V timing diagram, illustrating dual chamber operation utilizing a high rate sense window (Wenckebach mode), with a normal heart rate.

Referring now to FIG. 2A, there are shown parallel graphs of atrial (A) and ventricular (V) operation, under normal conditions. As explained below, the basic timing for the pacer system of this invention is from atrial signal to atrial signal, such that the pacer timing normally recycles upon a delivered atrial stimulus or a sensed P signal. The atrial graph of FIG. 2A presents normal operation, with a physiological atrial rate below the predetermined pacer rate limit. The P signals are shown as occurring substantially periodically, i.e., at a constant rate. Once each cycle a window W, sometimes referred to as the "Wenckebach" window, is illustrated, representing a range of time each cycle during which the pacer is enabled to sense P wave signals, and upon so sensing responds in a specific manner. The window W is also illustrated in the graph of time intervals shown in FIG. 2D. On the ventricular (V) graph, the ventricular simulus signals $V_{st}$ are shown, being positioned at a time T following each P wave signal.

Figure 2B:
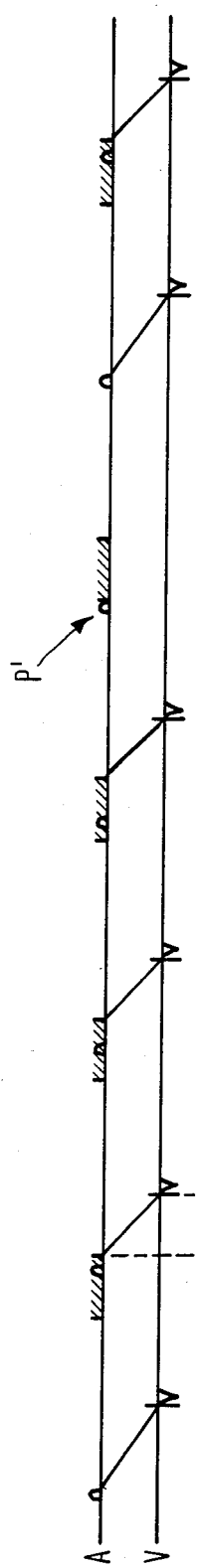
FIG. 2B is an A/V timing diagram, illustrating dual chamber operation where the natural atrial rate exceeds a predetermined maximum limit established by the normal atrial refractory period, with provision for maintaining the mean ventricular stimulus rate below the predetermined high rate limit and for maintaining the actual P-R (A-V) interval at an average value equal to the normal pacer A-V delay.

Referring to FIG. 2B, there is illustrated the pacer mode of operation when a high natural atrial rate is present, and specifically when the atrial rate exceeds the arbitrarily predetermined maximum rate limit. As illustrated, the first V stimulus occurs following a normal $T_{AV}$ interval after the sensed P signal. However, the next P signal is illustrated as falling in the window W. In the pacer mode of operation as described herein, the pacer timing is recycled at the end of the window W, following which a reduced AV interval, for example in the amount $T_{AV}$-W/2, is timed out. It is seen that, for such a physiologically natural high rate, the P signal proceeds "backwards" through the window until it appears prior to the start of the window. The first P signal to occur prior to the window, designated P', is ignored for purposes of synchronous operation, i.e., no ventricular stimulus is delivered thereafter. The absence of this ventricular stimulus reduces the mean, or average ventricular stimulus rate to a value below the predetermined maximum limit. Further, by reducing the timeout of the delay following the end of the window to the next delivered ventricular stimulus, the average delay between the natural P wave and the delivered ventricular stimulus $V_{ST}$ is maintained at about $T_{AV}$, which is the predetermined optimum value.

Figure 2C:
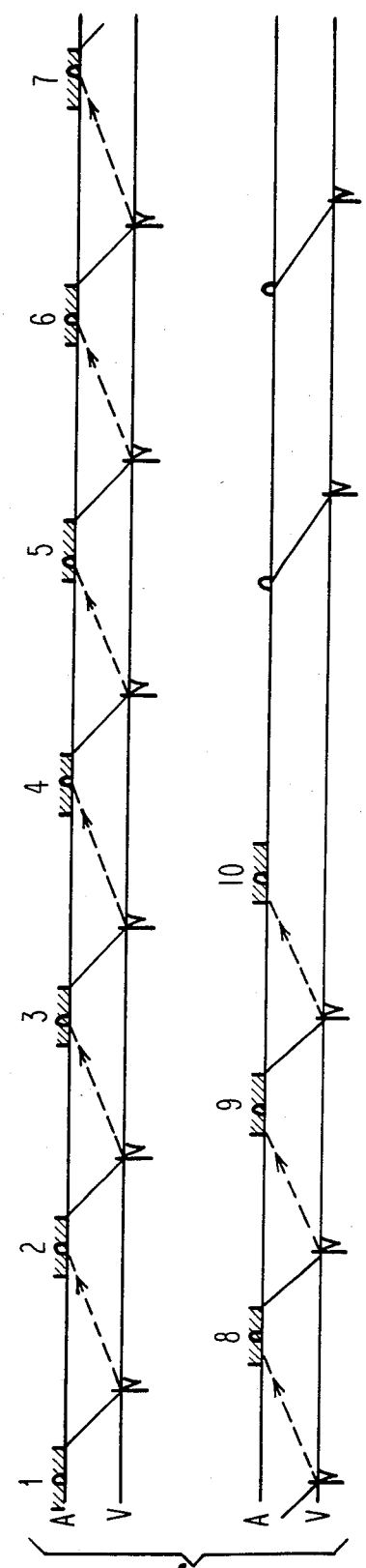
FIG. 2C is an A/V timing diagram, illustrating operation of the pacer during pacemaker supported tachycardia, as well as breakup of the tachycardia.

Referring now to FIG. 2C, there are shown curves illustrating the monitoring of pacemaker supported tachycardia, and the pacemaker response to breakup such tachycardia, in accordance with this invention. As described more fully below in connection with the flow diagram of FIG. 3A, whenever an atrial P signal falls within the Wenckebach window W, a counter is incremented, providing an indication of the successive number of P signals sensed to have fallen within the window. In the case of retrograde P waves resulting from the pacemaker ventricular stimulus pulses, each retrograde P occurs at substantially the same time interval following the delivered $V_{ST}$. Since time zero for the pacer cycle starts at the end of the window W, and not at the time of the sensed P signal, and since the retrograde conduction time from ventricle to atrium is substantially constant, each sensed retrograde P signal will fall in the window, which has been positioned to "see" such P wave. The timing of the window is such that retrograde P waves will fall within it, and be recognized as such. This is contrasted with the condition of physiological high rate atrial activity, as seen in FIG. 2B, where the sensed P signal shifts through the window after a number of cycles. As illustrated in FIG. 2C, P signals occuring within the window are counted up to an arbitrary number, e.g. 10, following which one V stimulus is skipped. Alternately, as illustrated in the preferred embodiment of FIGS. 3A and 3B, after the 9th P signal is counted, the window is closed the next cycle. Although a 10th retrograde P occurs during the window time, it is not sensed. It is important to note that the dropping of a single ventricular stimulus pulse is effective in terminating such pacemaker supported, or induced tachycardia, since no retrograde P can occur in the absence of a ventricular stimulus.

FIG. 2D is a series of graphs, illustrating the basic timeout intervals which are utilized by the pacemaker of this invention during each pacer cycle. It is to be understood, of course, that other intervals may be timed out, for other purposes, but only the intervals material to the invention as claimed are shown. The $T_{AV}$ interval is the normal AV delay, which is timed out after the occurrence of a P signal, i.e. at the beginning of a cycle which is designated at the top line by the letter "A". The time $T_{ar1}$ represents the end of the absolute atrial refractory period. After the timeout of $T_{ar1}$, the pacer looks for any P signal which might occcur, for the purpose of determining the presence of a PVC. For the purposes of this invention, a PVC, or Premature Ventricular Contraction, is defined as a sensed R signal which precedes any sensed P signal. The time $T_{ar2}$ is used to define the front end of the window W, which window is illustrated as terminating at time $T_{ar3}$, which is the normal atrial refractory period. $T_{ar3}$ sets the maximum atrial rate corresponding to which ventricular stimulus pulses are generated on a one-to-one timing basis, and also defines the end of the ventricular refractory period. The time $T_{atr}$ is an arbitrarily determined time between the end of the atrial refractory period and the end of the escape interval. As discussed below, this time is used to define a window $T_{ar3}$-$T_{atr}$ which is used, in one embodiment of this invention, to determine whether a sensed atrial beat is deemed to be physiological. As set forth below, if an atrial signal is sensed within the physiological $T_{ar3}$-$T_{atr}$ window, then the pacemaker enables the $T_{ar2}$-$T_{ar3}$ window for the next cycle. Last, the time $T_{aa}$ is the atrial escape interval, which also defines the pacer interval where there is a complete time out from one atrial stimulus to the next.

Figure 3A:
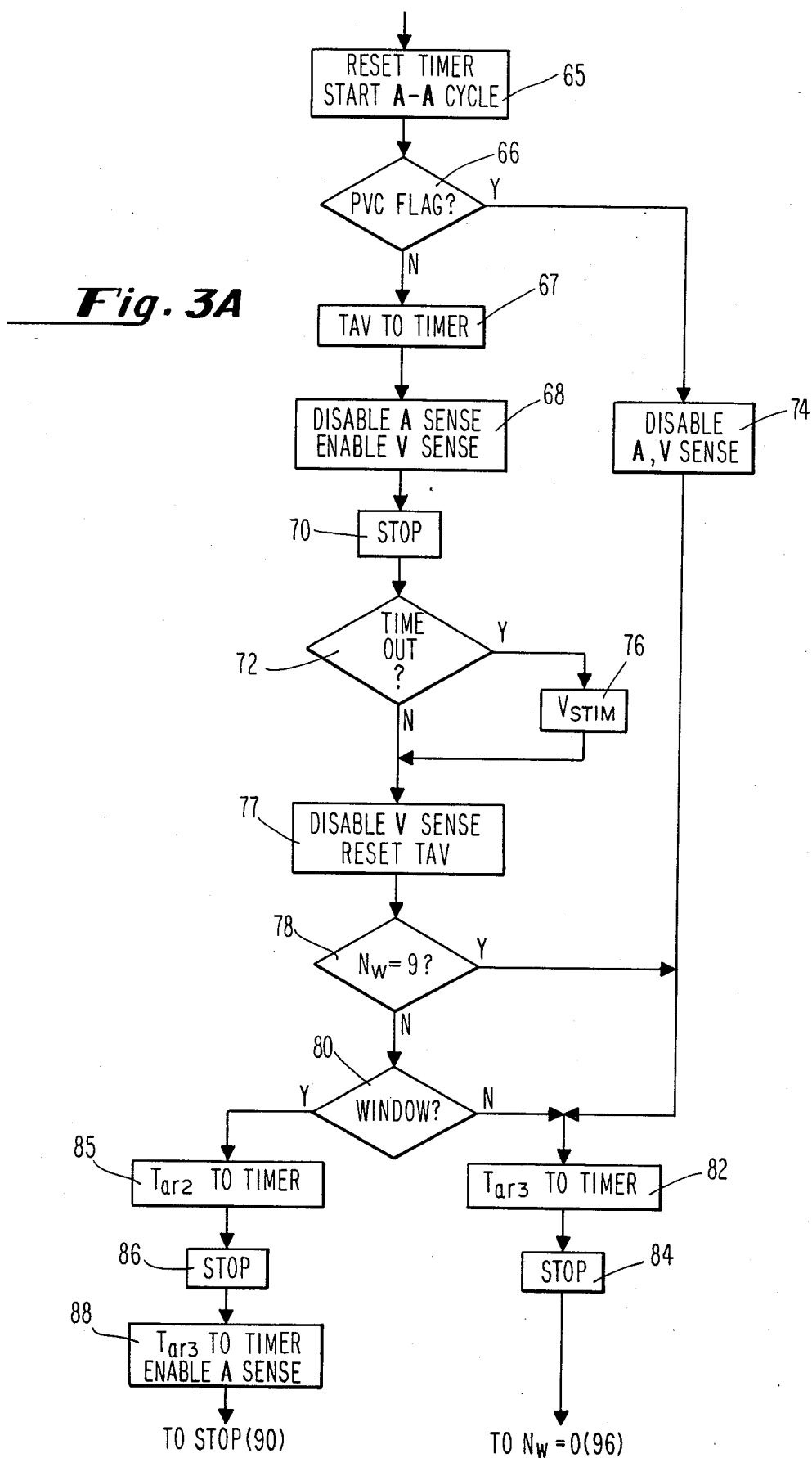
FIGS. 3A and 3B combined constitute a flow diagram showing the primary steps performed in the practice of this invention, during each pacer cycle. While the steps are illustrated as a software flow diagram, they can be performed by any equivalent hardware embodiment.
Figure 3B:
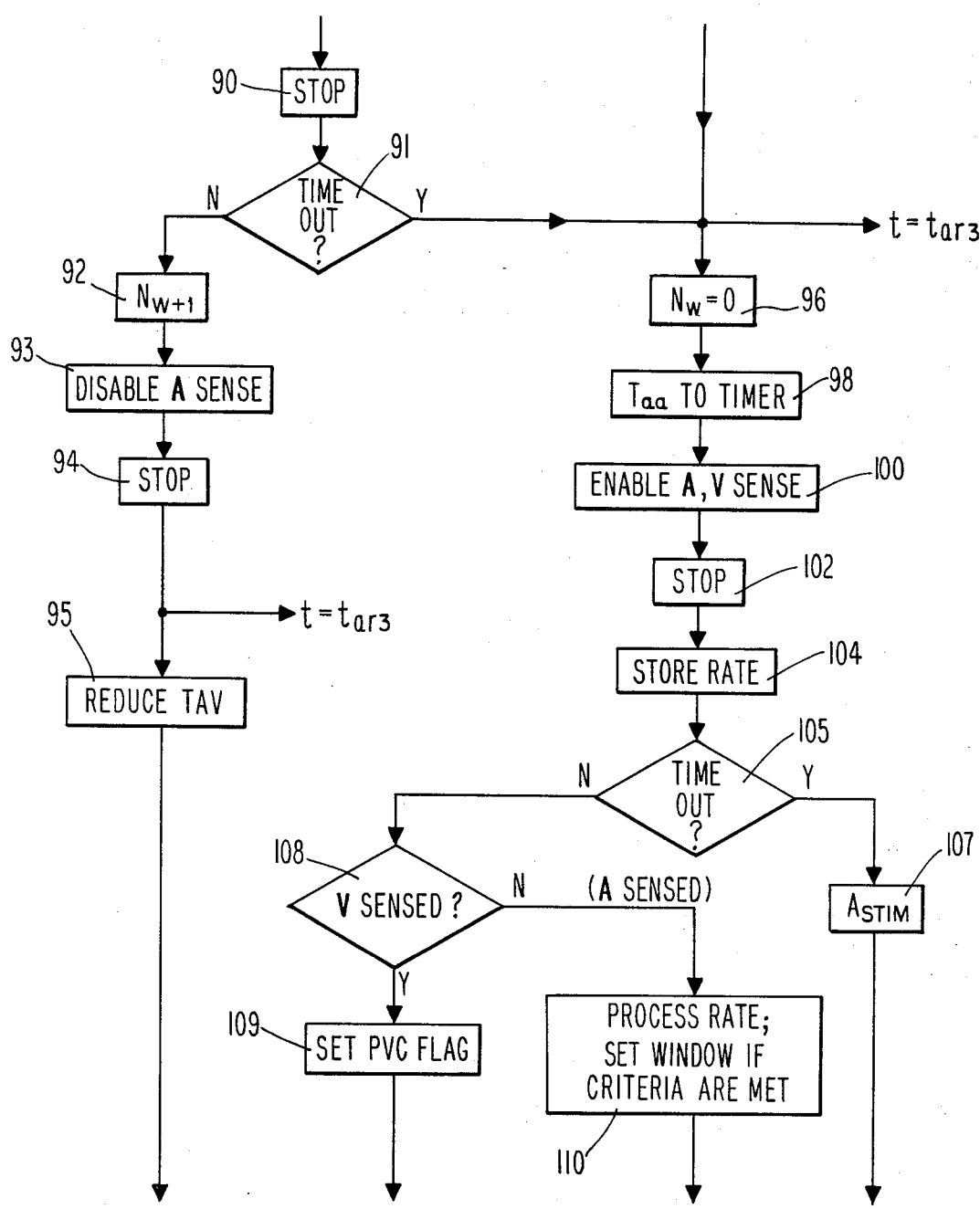

Referring now to FIGS. 3A and 3B, there is shown a flow diagram which represents the primary steps taken in the practice of this invention. This flow diagram is represented to illustrate steps taken under microprocessor control, i.e. this is a software flow diagram for the preferred embodiment. It is to be understood that this is a condensed flow diagram which illustrates only the steps necessary to set forth the preferred embodiment, and is not represented to be a complete flow diagram which illustrates all steps taken each cycle by the pacer. Clearly there are a lot of bookkeeping functions, well known in the art, and other operating functions which are performed each cycle, which steps need not be shown in order to illustrate the invention. Reference is made to co-pending applications Ser. Nos. 436,411, 436,457 and 436,454, incorporated herein by reference, for examples of other operations which may be carried out by the microprocessor controlled pacemaker.

Referring to the start of the flow diagram, at block 65 the pacer timer is reset, which represents the start of the A-A cycle. At block 66, it is determined whether the PVC flag has been set, i.e., whether there was a detected PVC last cycle. If yes, the A and V sense circuits are disabled at block 74, and the program branches to block 82. The PVC flag must be reset, and this can be done following block 66, or between blocks 98 and 100, for example. If no, it proceeds to block 67, where the stored value of $T_{AV}$ is sent to the timer, such that when the timer reaches a time $t=T_{AV}$ the microprocessor is re-started. Following this, at block 68 the A sense circuitry is disabled and the V sense circuitry is enabled, and the microprocessor stops (block 70) until the next event. At block 72, at which time the microprocessor has started to run again, it is determined whether the timer has in fact timed out to $T_{AV}$. If no, this means that a natural ventricular beat occurred and was sensed. If yes, the program branches to block 76, and causes the pacemaker to generate and deliver a ventricular stimulus. Following this, at block 77 the V sense circuitry is disabled, and $T_{AV}$ is reset to its normal value (in the event that it had a reduced value, as is discussed below). At block 78, a determination is made as to whether $N_W$, the number of consecutive P signals that have been sensed in the window W, if any, is equal to 9. If the answer is yes, meaning that 9 consecutive P wave signals have been sensed in the W window, this is an indication of stability of the V-A interval, caused by retrograde P waves, and thus of pacemaker induced or promoted tachycardia. In this event, the program branches to block 82. If $N_W$ does not equal 9, the pacemaker proceeds to block 80, and determines whether the window W is set. If the answer is no, the pacemaker proceeds to block 82, where $T_{ar3}$ is sent to the timer, and the microprocessor stops at block 84 to wait for a timeout at $t=T_{ar3}$. If, at block 80, it is determined that the window W is set, at block 85 $T_{ar2}$ is sent to the timer, and the microprocessor stops at 86 to wait for time $T_{ar2}$, the start of the window W. When this time occurs, the microprocessor starts again, and at block 88 sends $T_{ar3}$ to the timer and, enables the A sense circuitry, following which it stops at block 90 to await either the sensing of a P wave signal or the timeout of $T_{ar3}$.

As shown at block 91, if it is determined that there is timeout at $t=T_{ar3}$, the pacer branches to block 96. The pacer first determines whether $N_W$ is set to 0, and if so the window is reset; $N_W$ is then set equal to zero. However, if there was not a timeout, indicating that a P signal was sensed within the window W, the program branches to block 92, where $N_W$ is incremented to $N_W+1$. The A sense circuitry is then disabled at block 93, and the microprocessor stops at block 94 to await the timeout of t equal to $T_{ar3}$. At that time, which is the end of the window W, the pacer reduces the normal value of $T_{AV}$ at block 95, and recycles to block 65 where the timer is reset, to start a new cycle. The reduction in $T_{AV}$ is made because of the time delay between the natural occurrence of the P wave and the end of the window at $T_{ar3}$. If this time interval were not accounted for, the total A-V delay, or time between the atrial beat and the ventricular stimulus, would be longer than normal, a condition which the apparatus of this invention is designed to avoid. Although the reduction of $T_{AV}$ may be set arbitrarily by any factor stored in RAM or ROM, it is preferable to reduce $T_{AV}$ by one-half the window W, since the average delay from the sensed P wave to the end of the window will be W/2. Thus, for a window length of about 100 ms, the reduction is 50 ms. Alternately, the pacer can employ a correlation between TAV and AA time, e.g., TAV is proportioned to AA time in accordance with a programmable relationship.

Going back to block 96, which is reached when there is no window enabled or no P wave is sensed within the window, if, by only if $N_W$ equals zero, the window is reset and $N_W$ is then set equal to zero. Since no P wave has been sensed within the window there is no consecutive series of retrograde P waves sensed, meaning that the number of consecutive P waves is zero. At this time, the interval time t is $T_{ar3}$, the end of the normal atrial refractory period and also the end of the ventricular refractory period. Accordingly, the atrial escape interval $T_{aa}$ is sent to the timer at block 98, and both the A and V sense circuitry are enabled at block 100, prior to stopping the microprocessor at 102. The microprocessor is started again either due to the timeout, which means that an atrial stimulus is to be delivered, or due to a sensed signal, atrial or ventricular. The cycle rate is stored at block 104, and at block 105 it is determined whether there has indeed been a timeout. If yes, an atrial stimulus is delivered, as shown at block 107. If no, it is determined whether a ventricular signal was sensed. If yes, the flow diagram branches to block 109, where the PVC flag is set if the sensed ventricular signal occurred without a prior sensed atrial signal, which is defined as the condition of a premature ventricular contraction. If the answer in block 108 is no, this means that an atrial signal has been sensed, and the computer proceeds to block 110 to process the rate which has been stored at block 104.

The functions carried out at block 110 are designed to make a determination as to whether the early atrial signal represents an increased physiological rate, and thus whether the window W should be established. Note that if the rate simply jumps from a normal rate at a value somewhere below the predetermined maximum directly to a rate that falls within the window W, the atrial signal is not sensed since the window W is not enabled. This is the usual condition where the signal falls within the refractory period. It is, of course, desirable not to act upon an earlier sensed atrial signal where, for example, that sensed signal actually represents noise of some sort. In the process and apparatus of this invention, the pacer processes the rate to see if there has been an increase toward the predetermined maximum rate, which increase can be considered to be of a natural, or physiological origin. This can be done in several different ways, in the practice of this invention.

In accordance with a first technique, at block 110 the pacemaker examines to see if the last beat fell within the $T_{ar3}$-$T_{atr}$ window, or predetermined range of time. If so, this indicates an atrial beat at a rate higher then normal, but still below the predetermined maximum, and such beat is deemed to be physiological, meeting the predetermined criterion for setting the window W. In this case, the W flag is set, such that during the next cycle the pacemaker branches on the Y path at block 80. The time $T_{atr}$, which represents the upper limit of the physiological search window, can be set at any predetermined value as selected by the operator, and stored in memory. In another embodiment, the pacemaker may take the differential between the rate stored for the prior cycle and the most recent rate, or process the rate over a plurality of successive cycles, applying a predetermined algorithm to determine whether there has been an increase in rate which is deemed to be a physiological increase, whereby the criteria for setting the window are met. It is to be understood that the rate may thus be processed in any one of a number of different ways, the window being set or not set in accordance with whether the processed rate meets predetermined logical criteria.

The embodiment of FIGS. 3A and 3B presents, by way of example, a preferred embodiment of determining the stability of the V-A interval. This is shown as being done by counting the number of P signals that occur within the window, and after the count reaches a predetermined number altering the pacer operation so as to avoid a retrograde P wave, thereby breaking up the tachycardia. In the embodiment of FIGS. 3A and 3B, after the ninth consecutive P wave signal is sensed, a V stimulus is delivered at block 76, and then the pacer waits until the end of the normal refractory period at $t = T_{ar3}$ to enable sensing, i.e., it skips the window sensing. Under these conditions, if a tenth consecutive retrograde P wave occurred, it would not be sensed for timing purposes.

There have thus been described preferred embodiments of the dual chamber pacemaker of this invention, incorporating means for monitoring the V-A time response, and thus the V-A stability, in using a measure of this stability as a means for determining the pacemaker promoted tachycardia. Further, for high rate dual chamber operation, there is shown a means for optimizing synchronous operation at a mean ventricular stimulus rate which is below a predetermined maximum rate which maximum is a programmable parameter. For such high rate operation, the real time interval between the atrial heartbeat and delivered ventricular stimulus is maintained at about a constant value, even while maintaining the mean ventricular stimulus rate below the predetermined value. While specific flow diagram embodiments have been shown for the apparatus and method of this invention, it is to be understood that other procedures can be followed within the scope of the invention. Likewise, different hardware embodiments can be employed to carry out the essence of the invention, within the scope of the invention as claimed.

We claim:

1. A cardiac pacemaker having atrial terminal means for connection thereto of P signals representing atrial heartbeats and ventricular terminal means for connection thereto of generated ventricular stimulus Vst pulses, ventricular pulse generating means for generating and connecting said Vst pulses to said ventricular terminal means, atrial sensing means for sensing P signals connected to said atrial terminal means from the patient's heart,
    measuring means for measuring when a sensed P signal follows a connected Vst pulse by a V-A time which is within a predetermined range,
    counting means for counting the number of successive P signals having a V-A time within said predetermined range, and
    skipping means for causing skipping of sensing of the next P signal within said predetermined range following sensing of a P signal which is counted as the nth successive P signal by said counting means, where n is a predetermined number.

2. The pacemaker as described in claim 1, further comprising P rate means for determining a measure of the rate of sensed P signals, wherein said means for counting further comprises initiating means for initiating counting only when said P signal rate is determined to meet at least a predetermined criterion.

3. The pacemaker as described in claim 1, wherein said measuring means comprises window logic means for measuring when a sensed P signal occurs within a time window W corresponding to said predetermined range, and enabling means for enabling said window logic means as a function of a sensed physiological P signal within a physiological time window corresponding to a lower range of rates then that of said window W.

4. The pacemaker as defined in claim 3, having pacemaker timing means for timing out pacemaker cycles, said timing means being re-cycled to initiate a new pacing cycle normally upon the occurrence of each atrial signal, and means for modifying said timing means to initiate a new cycle only at the end of said time window W when a P signal is sensed within said time window W.

5. The pacemaker as described in claim 4, comprising means for normally timing out an A-V interval $T_{AV}$ following sensing of a P signal, and means for causing said ventricular pulse generating means to generate a stimulating pulse at the end of the timed out $T_{AV}$, further comprising means for reducing $T_{AV}$ to less than said normal $T_{AV}$ following the sensing of a P signal within said time window W.

6. The pacemaker as described in claim 5, wherein $T_{AV}$ is reduced by about one-half the time of said time window W when it is reduced.

7. The pacemaker as described in claim 3, comprising means for detecting the occurrence of a PVC, and means for disabling said window logic means following the occurrence of a PVC.

8. The pacemaker as described in claim 1, comprising means for processing sensed P signals having rates below a predetermined maximum rate corresponding to the end of the normal atrial refractory period, and further having means for adjusting said maximum rate as a predetermined function of such sensed processed P signal rates.

9. The pacemaker as described in claim 1, comprising second window means for timing out an evaluation window, and wherein said initiating means comprises means for determining when a sensed P signal appears within said evaluation window.

10. The pacemaker as described in claim 9, wherein said measuring means comprises first window means for timing out a first time window corresponding to said predetermined range, said second time window following said first time window.

11. A dual chamber cardiac pacemaker, having means for sensing atrial heartbeats and means for delivering ventricular stimulus pulses, comprising
    monitoring means for monitoring the time relationships between said ventricular stimulus pulses and the respective succeeding atrial heartbeats of the patient, means for storing data reflective of a plurality of said monitored time relationships, and means for determining the occurrence of pacemaker mediated tachycardia in accordance with said data, and
    means for altering pacer operation in response to the determining of a said occurrence.

12. The dual chamber pacemaker as described in claim 11, wherein said means for altering normal pacer operation inhibits delivery of a ventricular stimulus pulse at the normal A-V time following a sensed atrial heartbeat signal when there has been a determination of pacemajer mediated tachycardia.

13. A cardiac pacemaker having cyclical means for cyclically sensing P signals representative of a patient's atrial heartbeats and generating stimulus pulses for delivery to a patient's ventricle, further comprising
    means for measuring the stability of the V-A intervalbetween a delivered ventricular stimulus pulse and the next succeeding atrial heartbeat and for determining the existence of tachycardia as a predetermined criteria of said measured V-A internal stability, said means for measuring including means for measuring the occurrence of a plurality of P signals each occurring within a predetermined time window following a respective prior ventricular stimulus pulse, and means for changing the operation of said cyclical means over at least a portion of a cycle following determination of the existence of tachycardia.

14. The pacemaker as described in claim 13, wherein said means for changing controls said cyclical means to skip generation of a stimulus pulse which would normally be generated following sensing of a P signal.

15. The pacemaker as described in claim 13, wherein said means for changing controls said cyclical means to disable sensing of the next normally due P signal if it occurs at a V-A interval with a predetermined time range.

16. The cardiac pacemaker as described in claim 13, in combination with an atrial lead for connnection directly to a patient's atrium, and a ventricular lead for connection directly to the patient's ventricle.

17. The cardiac pacemaker as described in claim 16, comprising control means for operating in A-V synchronous operation and having program means for receiving program signals to place said pacemaker into A-V synchronous operation.

18. The cardiac pacemaker as described in claim 13, wherein said means for measuring stability of the V-A interval comprises means for measuring said interval over a plurality of successive cycles of operation.

19. The cardiac pacemaker as described in claim 18, wherein said means for measuring includes means for determining the average value of said V-A interval over a predetermined number of cycles of operation.

20. The cardiac pacemaker as described in claim 17, wherein said means for measuring comprises means for determining the occurrence of V-A intervals within a predetermined time range corresponding to pacemaker mediated tachycardia.

21. A dual chamber cardiac pacemaker for pacing a patient in at least an A-V synchronous mode, having means for sensing P signals, A-V timeout means for timing out an A-V delay following a sensed P signal, said A-V delay normally being a predetermined time $T_{AV}$, and means for generating a ventricular stimulus pulse for delivery to the patient at the time out of a said A-V delay, further comprising means for timing out an atrial refractory period following each sensed P signal, which atrial refractory period corresponds to a predetermined maximum heartbeat rate; and control means for controlling said A-V timeout means (i) to delay initiation of timing out said A-V delay to the end of said atrial refractory period whenever a P signal is sensed before the end of said atrial refractory period, and (ii) to reduce the length of said A-V delay to a time less than $T_{AV}$ following each said delay of initiation.

22. The pacemaker as described in claim 21, wherein said control means establishes a P sense window for sensing said P signals from the patient's heart during a predetermined time period W preceding the end of said atrial refractory period, and said A-V delay timeout is reduced to about one-half W so that the A-V delay equals about $T_{AV}-W/2$.

23. The pacemaker as described in claim 22, comprising stability means for monitoring the occurrence of P signals within said P sense window, and for determining the existence of patient tachycardia due to retrograde P waves as a function of said stability monitoring.

24. The pacemaker as described in claim 23, comprising process means for processing the sensed P signals which have rates lower than said predetermined maximum heartbeat rate, and for enabling said control means to reduce the length of said A-V delay as a function of said processing.

* * * * *